United States Patent
Hunziker et al.

(10) Patent No.: US 9,606,094 B2
(45) Date of Patent: Mar. 28, 2017

(54) PORTABLE ELECTRONIC DEVICE WITH IMPROVED CHEMICAL SAMPLING

(71) Applicant: Sensirion AG, Stafa (CH)

(72) Inventors: Pascal Hunziker, Mannedorf (CH); Felix Mayer, Stafa (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 14/160,805

(22) Filed: Jan. 22, 2014

(65) Prior Publication Data

US 2014/0223996 A1  Aug. 14, 2014

(30) Foreign Application Priority Data

Jan. 31, 2013 (EP) .................................. 13405026

(51) Int. Cl.
*G01N 33/00* (2006.01)
*H04M 1/21* (2006.01)

(52) U.S. Cl.
CPC ..... *G01N 33/0031* (2013.01); *G01N 33/0075* (2013.01); *H04M 1/21* (2013.01); *H04M 2250/12* (2013.01)

(58) Field of Classification Search
CPC ........... G01N 33/0031; G01N 33/0075; G01N 21/274; G01N 33/24; G01N 2201/12753; G01N 2021/855; H04M 1/21; H04M 2250/12; H04M 2250/22; H04M 1/72569; G08B 21/22
USPC .................................... 73/31.01, 23.2, 31.05
See application file for complete search history.

(56) References Cited

U.S. PATENT DOCUMENTS

| | | | |
|---|---|---|---|
| 5,316,950 A * | 5/1994 | Apitz ................... | G01N 21/274 422/82.07 |
| 6,053,030 A * | 4/2000 | Whynall et al. ............... | 73/23.2 |
| 6,858,182 B1 * | 2/2005 | Ito et al. ....................... | 422/416 |
| 7,636,047 B1 * | 12/2009 | Sempek ................. | G08B 21/22 340/572.1 |
| 8,254,699 B1 | 8/2012 | Zhao et al. | |
| 2004/0050188 A1 * | 3/2004 | Richards et al. ............ | 73/866.3 |
| 2004/0075140 A1 * | 4/2004 | Baltes et al. .................. | 257/347 |
| 2004/0081582 A1 * | 4/2004 | Brooke ........................... | 422/62 |
| 2006/0058697 A1 * | 3/2006 | Mochizuki et al. ......... | 600/532 |
| 2006/0116175 A1 * | 6/2006 | Chu ................... | H04M 1/72569 455/567 |
| 2009/0164141 A1 * | 6/2009 | Lee ................................ | 702/30 |
| 2009/0268201 A1 * | 10/2009 | Call ............................. | 356/338 |

(Continued)

FOREIGN PATENT DOCUMENTS

WO        2011135476        11/2011

*Primary Examiner* — Hezron E Williams
*Assistant Examiner* — Marrit Eyassu
(74) *Attorney, Agent, or Firm* — Cooper & Dunham LLP

(57) ABSTRACT

A portable electronic device and a related methods are described using an integrated chemical sensor linked to a chemical sensor processing unit and being sensitive to the concentration of a component in a sample of air and one or more contextual sensors not including chemical, temperature and humidity sensors, wherein output from the contextual sensors is linked to a local or remote interpretation processor generating a constraint or correlation set transferred to the chemical sensor processing unit for use in determining a result of a chemical measurement as performed by the chemical sensor.

14 Claims, 3 Drawing Sheets

(56) References Cited

U.S. PATENT DOCUMENTS

| | | | |
|---|---|---|---|
| 2010/0234062 A1* | 9/2010 | Ito | G01C 17/30 455/550.1 |
| 2012/0191349 A1 | 7/2012 | Lenz et al. | |
| 2012/0282885 A1 | 11/2012 | Hamed et al. | |

* cited by examiner

PORTABLE ELECTRONIC DEVICE WITH IMPROVED CHEMICAL SAMPLING

FIELD OF THE INVENTION

The present invention relates to a portable electronic device such as a mobile phone, tablet and the like with an integrated chemical sensor with the sensor being located in the exterior shell or housing of the device.

BACKGROUND OF THE INVENTION

Portable or mobile devices originally introduced as mobile phones or electronic agendas become more and more ubiquitous. As the processing power of their internal processors grows and equally the bandwidth for communication with stationary processors, such portable devices take on more and more the role of multi-purpose tools available to consumers and specialist users alike.

It has been recognized that portable devices can benefit from the presence of sensors capable of providing a chemical analysis of materials brought into contact or the vicinity of the device. Whilst there are many possible applications for such sensors, it suffices to consider for example the analysis of air surrounding the portable device. Such an analysis can be useful for multiple purposes such as testing for hazardous gases, breath analysis for general medical purposes or driving fitness, and the like.

However, the chemical analysis of an air sample is recognized as a very difficult problem. This problem is compounded by the limited size of portable equipment, which in turn limits the size and number of the sensors which can be housed inside the device. Furthermore, if the device is designed as a general purpose device the possible number of different samples taken and the conditions under which the sampling is performed become virtually unlimited.

One possible solution to this problem is seen in using a combination of several sensors to measure physical parameters which are known to have a relevance for the sampling or testing. For example, the chemical sensor can be made up of several chemical sensors or arrays of chemical sensors with different, i.e. orthogonal, sensitivities that can be used to improve the capacity of the sensor to distinguish between different compounds. Other physical sensors are temperature and humidity sensors, which under certain conditions can be used to improve the chemical measurement.

However, as stated above the assembly of a plurality of physical sensors is difficult to implement in the often limited space afforded to sensors in portable devices. Further limits are posed by the energy consumption of such a plurality of sensors, which in a general purpose portable device have to compete for the limited amount of battery power with other functions often considered more fundamental such as telecommunication, imaging, video and music capture and reproduction.

In view of the above problems it is seen as an object of the invention to provide a portable electronic device and related methods for increasing the accuracy of a chemical sensing process as performed by a sensor located within its housing.

SUMMARY OF THE INVENTION

Hence, according to a first aspect of the invention, there is provided a portable electronic device, preferably with telecommunication capabilities to allow for data and/or voice communication via private or public networks, enclosed in a housing having preferably an air duct with an opening to the exterior of the housing and at least one chemical sensor connected to a chemical sensor control and processing unit receiving further input from contextual sensors.

Contextual sensing devices are understood to exclude other chemical sensors, temperature and humidity sensors. The excluded sensors can be regarded as physical sensors with a direct relevance to the chemical sensing process and are not within the scope of the present invention. In turn, contextual sensors are understood to be sensors generating an output the relevance of which to a chemical sensing process is less direct and often requires further conversion or interpretation to provide useful parameters for the chemical sensing process.

Contextual sensors within the meaning of the present invention can be selected from a group including picture or video cameras, IR sensors, acoustic microphones, location sensors (GPS), brightness sensors, ultrasound sensors, proximity sensors, acceleration sensors, Bluetooth receivers, EM wave antennae and orientation sensors, whereby these sensors are preferably integrated into the same housing as the chemical sensor or, alternatively or in addition, sensors which can communicate directly or indirectly, i.e. over a common server, with the portable device. When integrated into the same housing, the contextual sensors can be located at the exterior of the duct housing the chemical sensor. According to this aspect of the invention, it can be seen as an object to use sensors often already included for other purposes into a portable electronic device in a novel fashion to extract data from their measurements, which can be then be used to restrict the possible interpretations of a measurement made by the chemical sensor including any associated other physical sensors.

However, contextual sensors are not likely to generate a measurement which can be used directly to improve the chemical measurement. The direct output of the contextual sensors requires typically a processing by an intermediate interpretation processor before providing a usable input to the recognition processor of the chemical sensor. The interpretation processor can include an image recognition processor, a speech or sound recognition processor, a motion or orientation recognition processor or a general scenario or event interpretation processor providing an additional interpretation of the objects sampled by the chemical sensor and/or conditions under which the chemical sampling is performed.

As the current capabilities of processors in mobile devices are in general not sufficiently powerful to provide the complex interpretation to convert the signals derived from a contextual sensor into an input to the recognition processor of the chemical sensor, some parts or all of the interpretation processor can be implemented on remote computers or servers. In this case, the measurement result of a contextual sensor, for example signals representing an image, is sent using the telecommunication capability of the device, then processed on a remote computer, server or cluster of servers or computers before an interpreted result is sent back to the requesting portable device.

As the processing powers within a portable device grow, it is however anticipated that more of this remote processing will be performed locally, i.e. using the resources and computing powers of the portable device itself. The degrees as to which a processing operation of the interpretation processor and/or the recognition processor are handled locally or remotely, is much a matter of available processing power, battery power and communication bandwidth and hence subject to change in line with general advances in portable signal and data processing technology.

The interpretation processor has preferably access to a database which links an interpreted measurement as provided by a contextual sensor or sensors with a chemical interpretation which in turn is provided as input to a chemical recognition processor. The chemical recognition processor will alter a result derived from the signals received from the chemical sensor to match the constraints or correlations as imposed by the input from the interpretation processor and, hence, from the output of the contextual sensors.

The chemical recognition processor can further include a precision unit. The precision unit is programmed to monitor a preliminary output of a result of the local processing unit for the chemical sensor. This preliminary output is based on the result of a measurement by the chemical sensor alone or in combination with other physical sensors of the portable device. Based on the preliminary result and a confidence measure associated with it, the precision unit performs a test to decide whether or not to request input from contextual sensors. The precision unit or a part of the interpretation processor can either access any measurement and values from contextual sensors as stored in the device or initiate the activation of a contextual sensor to perform additional contextual measurements, if deemed necessary based on the outcome of the test.

A preferred chemical sensor includes a sensor material, preferably in form of a layer, also denoted as receptor layer, to which an analyte may bond to and as such modify an electrical property of the sensor material such as its electrical conductance, e.g. metal oxide chemical sensors. It can also include a plurality of different sensors or an array of similar sensors. In such a sensor array, each sensor cell may provide a layer of a material exhibiting different absorption characteristics such that each cell of the sensor array may specifically be sensitive to a different analyte and as such may enable the portable electronic device to detect the presence or absence or concentration of such analyte.

A preferred sensor is combined with a least part of its control and read-out circuit onto a single semiconductor substrate. In a preferred variant this circuit is a CMOS circuit.

The portable device can be a smart phone, a handheld computer, a laptop, an electronic reader, a tablet computer, a game controller, a pointing device, a photo or a video camera, a digital music player, an electronic wrist watch, a headset or a computer peripheral. Its housing is typically a shell of metal, glass, or plastic material and can be assembled as a unibody or from several parts. Enclosed in the housing are typically processors, drivers for parts such as screens, antennae, cameras, microphones and speakers as well as batteries to provide power to the device and its parts. A screen is typically arranged as a part of the housing or mounted behind a transparent window of the housing.

The duct acts as confinement for the air inside the housing and can take the shape of a tube or channel formed as part of the housing or as a separate part connected to an opening in the housing. It can be a single straight or curved duct.

The opening itself can be a dedicated opening thus exclusively connecting the chemical sensor to the outside. However, given that the manufacturers of portable electronic devices strive to maintain the housing as a good protection against humidity and water, it is seen as advantageous that the opening is shared with at least one further component of the portable device requiring a similar connection to the exterior, such as a loudspeaker, a microphone or a camera. The opening can further be protected by a grill or a membrane to prevent bigger particles or unwanted components of the air from entering or blocking the duct.

A further aspect of the invention pertains to a method of improving the results of a measurement of a chemical sensor within a portable device using the output of contextual sensors as described above to enhance the accuracy of the chemical measurement.

The above and other aspects of the present invention together with further advantageous embodiments and applications of the invention are described in further details in the following description and figures.

DETAILED DESCRIPTION

Figure 1A:
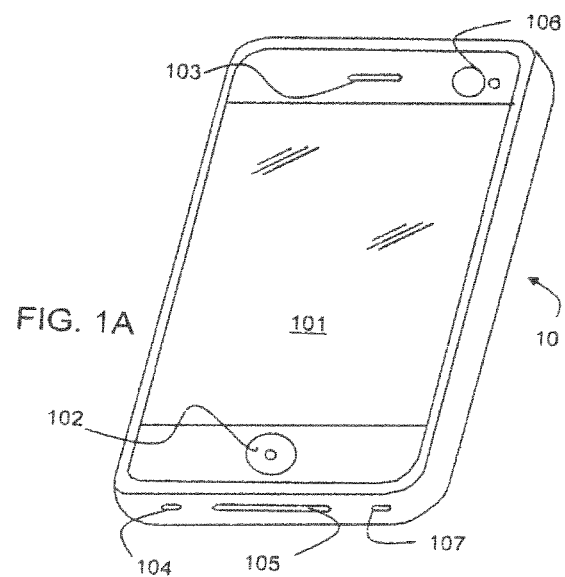
FIG. 1A is a perspective view of a portable electronic device.

The device of FIG. 1A is a portable electronic device such as a mobile phone. The housing 10 of the mobile phone includes a front side with a screen 101 and elements like buttons 102 to let a user interact with the phone. Also shown on the front side is an opening 103 for a loudspeaker. Further openings 104,105 are located at a lower side wall of the housing 10. It is well known to mount components like microphones and loudspeakers behind such openings. The phone includes one or two cameras 106, and internally additional sensors (not shown) such as location sensors or GPS, and acceleration and orientation sensors in a manner well known.

Figure 1B:
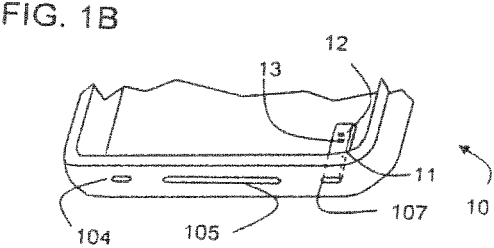
FIG. 1B is a schematic view into part of the housing of the device of FIG. 1A.

Another opening 107 is located at the lower side wall. As shown in FIG. 1B the opening 107 is linked to a tubular duct 11 passing through the interior of the housing. A chemical sensor 12 and a humidity sensor 13 are both mounted along the duct 11 such that the sensitive areas of both sensors are essentially exposed to air of the same composition entering the duct through the opening 107. The actual size and shape of the duct 11 depends on the volume available and the nature of the chemical sensor 12 and the humidity sensor 13 can vary, but given the physical constraints of portable mobile devices the area of the opening is typically in the range of less than 10 square millimeters and in the present example actually about less than 3.1 square millimeters.

Figure 2:
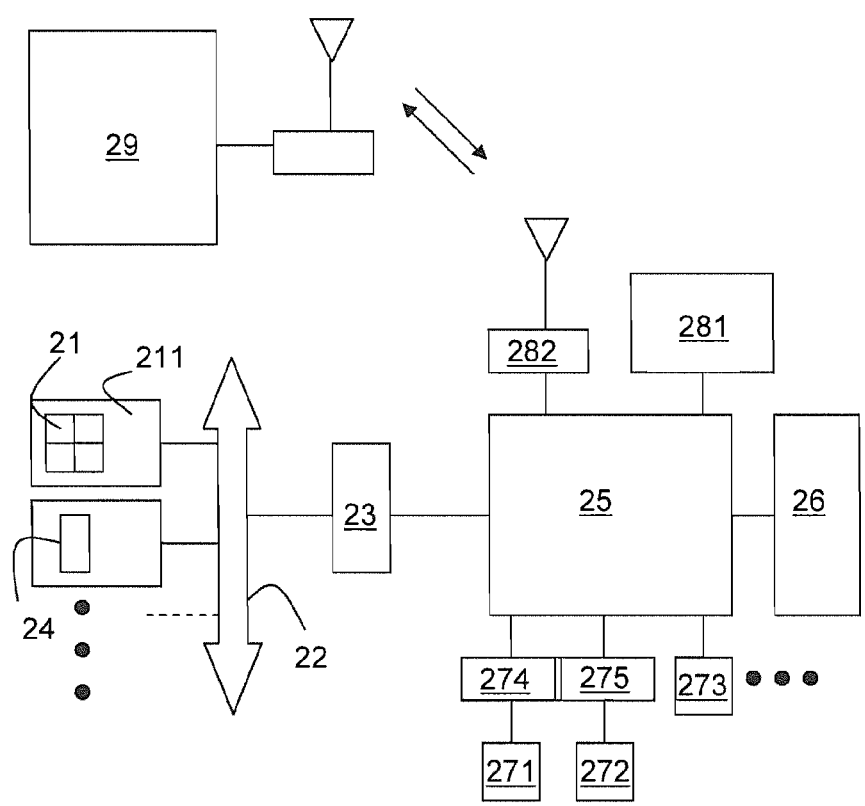
FIG. 2 is a block diagram with components of a portable device in accordance with an example of the invention.

FIG. 2 shows a block diagram with the most important components of the portable device. In particular, the device includes a chemical sensor 21 integrated as part of a CMOS substrate 211 which has CMOS circuitry to control the basic functions and the basic readout of the sensor. The CMOS circuit can include for example the driver to switch the sensor and its heater on or off as well as A/D converters and amplifiers and an I2C bus controller to exchange data on an I2C bus 22. The I2C bus connects the sensors with a sensor hub 23. A further humidity and temperature sensor 24 is also linked to the I2C bus 22. The chemical sensor 21 can be for example a single sensor, such as a metal oxide type sensor, or an array or assembly of several sensors. The chemical sensors can be either of the same type of metal oxide sensors but with a different sensing material or, either alternatively or in addition, sensors based on a different sensing principle.

The sensor hub 23 provides a control and processing unit for more complex control and read-out functions of the chemical sensor 21 based on signals sent to or extracted from, respectively, the on-chip CMOS circuitry.

Further control and read-out functions can also be performed by the central processing unit (CPU) 25 of the portable device, which in turn has read/write access to a memory 26, which can include static or volatile memory or both as known in the art. The memory 26 typically stores the operating system of the device and can also be used to store programs specific to the operation of the sensors of the portable device.

In addition to the specific sensors as described above, the CPU is also connected to one or more sensors 271, 272, 273 which typically operate independently of the operations of a chemical sensor. These sensors provide other functionality or capabilities of the portable device, thus creating an independently useable output of the portable device with no direct connection to the chemical sensor 21. One of these contextual sensors is for example the camera 271 or the microphone 272 also shown as the camera 106 and the microphone 104 of FIG. 1. Other examples are location, acceleration and orientation sensors. The contextual sensors 271, 272, 273 communicate with the CPU using their own interface units 274, 275, or via the sensor hub 23, respectively, which operate typically in complete independence of the chemical sensor 21.

The device includes further well known input/output units 281 such as a touch sensitive display, virtual or physical keyboards and gesture tracking devices etc. The portable device as shown has a telecommunication circuit 282 comprising an antenna, driver circuits and encoding and decoding units as are well known in the art. Using such a telecommunication circuit and a network interface unit NIU 282, the device can connect to remote data processing and storage facilities 29 as shown.

Figure 3:
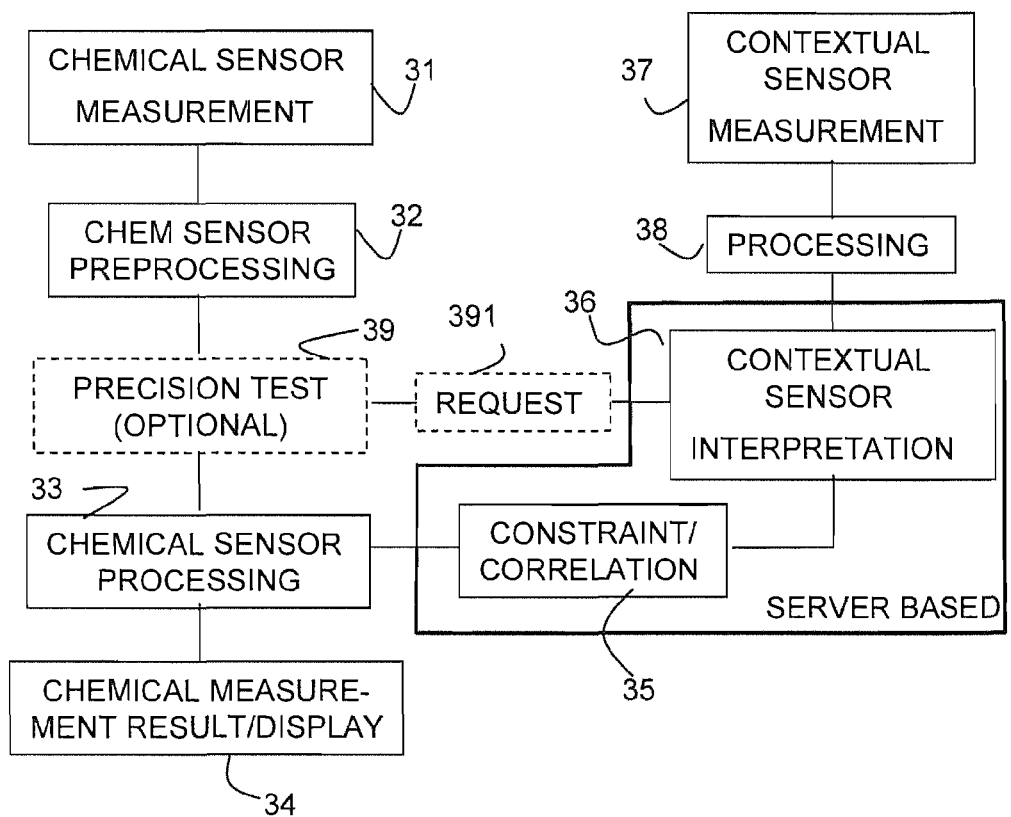
FIG. 3 illustrates processing steps in accordance with an example of the invention.

Exemplary operation modes of the above device are described in the following making further reference to the steps of the flowchart of FIG. 3.

A measurement in accordance with an example of the present invention includes a measurement 31 performed by the chemical sensor. In case of a metal oxide sensor, the sensor is for example heated using internal heating elements to its operating temperature in preparation for the measurement. During the measurement 31 an analyte being part of the air and entering into the housing through the duct reacts on the surface of the sensor causing a shift in the electrical resistance of the sensing material. This shift is measured, amplified and filtered and communicated as a first set of signals, which for the purpose of the present descript is referred to as raw data, via the I2C bus to the processing unit of the sensor hub.

In the processing unit the raw data is in a further step 32 processed to extract a first set of processed data referred to herein as chemical feature vector. At this level of signal processing the chemical feature vector represents the signal which can be for example used as input for a chemical processing unit 33 including for example a mathematical sensor model. The chemical processing unit 33 provides as output 34 a concentration value or a composition spectrum of the analyte. The sensor model can be part of the sensor hub 23 or the CPU 25 (see FIG. 2). The sensor model can take inputs from the temperature and humidity sensor 24 to further characterize the conditions under which the chemical measurement 31 was taken in as far as temperature or humidity influence for example the performance of the chemical sensor 21.

The processing unit receives also inputs, such as correlations or constraints 35, derived from an interpretation processing step 36, which in turn uses input from one or more of the contextual sensor measurements 37. To perform the contextual sensor measurements 37 is per se well known as are all the components and processing steps 38 required to operate the contextual sensors 271,272,273. Their independent functions within the operation of the portable device are not considered relevant for the purpose of the present example operations. However, the interpretation processor has access to the output of a contextual sensor making use of its (independent) components and functions.

In case of a camera 271, the output can be signals representing an image or a sequence of images. In case of a microphone the output are signals representing noises and spoken words. In case of a GPS unit the output can be a representation of a geographical location of the portable device or a sequence of locations. In the case of accelerometers etc the output can consist of signals representing current or past orientations or movements of the device.

The purpose of the interpretation processing step 36 is to convert the inputs as provided by one or more of the contextual sensors into an input such as a correlation or constraint, compatible with the processing unit linked to the chemical sensor. This conversion can be a complex process using potentially large data storage systems and powerful computing units. Even though it is feasible to have these units as part of a portable device at least as far as special or simplified cases are concerned, a more general implementation such as illustrated in the present example makes use of the telecommunication capabilities 282 of the device and hence of the remote data processing and storage facilities 29 as shown in FIG. 2.

The process to derive a constraint is described in further details referring to specific exemplary uses of contextual sensors.

In the case of the camera, image data can be used to extract information about the object sampled by the chemical sensor and/or the environment in which the sampling takes place. The extraction can use any of the known image recognition methods available such as for example described in U.S. Pat. No. 8,254,699 to Google Inc. The output of the image recognition process is a high level description of the content of the image.

The high level description of the image content can be used as address to a constraint vector or a group of constraint vectors stored in a digital library or generated on-the-fly using a set of predefined steps. For example identifying the image of specific fruit such as a banana in an image taken at the location of the sampling can result in a constraint vector representing the response or signature of the chemical sensor in the presence of ethylene. The known signature can in turn be used as a constraint in an analysis of the measurement of the chemical sensor thus limiting the variables to be determined. Alternatively the response or signature of the chemical sensor in the presence of ethylene can be used to design a filter applied to the measurements of the chemical sensor.

Both methods are well established methods in signal processing. They can include any of the known routines for complex data analysis including but not limited to Principal Component Analysis, Linear Discriminant Analysis and the like or neural network based tools such as Self-organizing Maps, Back Propagation, pattern recognition routines etc. These and similar methods known per se can be used either to enhance the sensitivity of the filter for an expected result, which in the example would be for the expected presence of ethylene, or to remove the expected signals to increase the accuracy with which other components can be identified.

Given sufficient processing capabilities the above steps can be extended to two or more objects recognized by the image processing unit and linked to a set of constraints.

In the same way the image can also used to identify the state of an object. For example, a fruit can be identified as having certain coloring indicating how far its ripening process has progressed. This information can again be linked to a certain chemical emission pattern of such a fruit and the expected response to it by the chemical sensor. In another example, during the chemical sampling of a fluid, image recognition may show the development of bubbles. This recognized state on the image can be linked to the presence of carbon dioxide in the air above the fluid.

A microphone can be used in a similar manner using either a local processing unit, i.e. a processor present in the portable device, or a remote processor. For the purpose of identifying words spoken by a user or registered randomly from speech uttered in the vicinity of the portable device, known speech recognition can be used to identify one or more objects which contribute to the sample as measured by the chemical sensor. The more advanced portable devices available today already have speech recognition capabilities, which can be adapted for this purpose making for example use of their application programming interfaces (API) as published.

The presence of characteristic noises such as car engine noise etc. can be identified and processed for noise recognition using for example spectral analysis and any of the statistical routines referred to above. Any sound identified can then be linked a typical chemical emission profile of a car engine as constraint for the processing of the chemical sensor signals.

General location information as provided by an internal location sensor, such as the widely used GPS sensor, can also create constraints representing the chemical response typical for the chemical emissions likely to be encountered. Examples for such location specific emissions encountered for example on or near a busy road are the typical components of car exhaust fumes such as NOx, CO and others. Knowledge of prevalent vegetation or spices etc. at a location identified can equally be used for generating a constraint.

The contextual sensors can also be applied to provide information on the sampling process. Motion, orientation or inertia sensor can for example be evaluated and time correlated with the chemical measurement using an internal clock signal common to both measurements as provided for example by the internal clock of the portable device. This correlation can be used to remove uncertainties or false measurements from the results of the chemical measurement. For example, the motion sensors of the portable device can indicate its movements between two different locations within the time period used for sampling. The interpretation processor can then identify this motion and issue a constraint or correlation. The chemical processing unit can process this constraint or correlation so as to split the chemical measurements into two sets each representative of a different measurement in order to interpret the measurements. Without such a correlation, the two distinct measurements would be interpreted as a single measurement and for example averaged resulting in an inaccurate result.

The contextual sensors including IR or proximity sensor can also be used to derive contextual information on the sampling process such as distance to the sample or orientation of the duct housing the chemical sensor to the sample. These information can be used in a model of the chemical sampling process to estimate distortion and dilution effects introduced by the specific conditions prevailing at the time of the sampling.

The addition of the contextual sensors and the interpretation processor to the chemical measurement can be made optional using for example a setting which can be selected by the user. Alternatively, this step 39 can be automated based for example on the accuracy or uncertainty of the chemical measurement 31. For this purpose the chemical sensor processor can be designed to generate together with the actual result for example a probability chart using a statistical analysis of the result and other results which nearly match the measured signals. With a threshold test or by using other predefined conditions, the processing unit can issue a request 391 for the addition of contextual sensor measurements to the actual chemical measurement. The automated process 39,391 has the advantage that the contextual sensors 271,272,273 are only activated when needed, thus preserving battery power compared to a system where the contextual sensors are immediately activated with the initiation of the chemical sensor 21.

The above described steps and particularly the automated addition of contextual sensors can be further refined with the use of the contextual sensors 271,272,273 in a pre-capture mode. The mode can be linked to an initiation of the chemical sensors by automatically activating one or more contextual sensors and storing the output of the contextual sensors temporarily in an appropriate storage on the device. The storage can be the memory used to store the output of the contextual sensor in its respective normal operation mode. In case a chemical measurement requires an evaluation assisted by these contextual sensors, the pre-captured signals can be used for the steps as described above. Using this pre-capturing, it is ensured that contextual sensor measurements are available which precede the actual chemical measurement.

While there are shown and described presently preferred embodiments of the invention, it is to be understood that the invention is not limited thereto but may be otherwise variously embodied and practised within the scope of the following claims. For example, it is possible to use sensors external to the portable device as contextual sensors. Such external sensors can be the contextual sensors of a second portable device in the vicinity of the portable device or, more generally, any sensor in the spatial or temporal surrounding of the portable device, the output of which can be linked to the interpretation processor.

The invention claimed is:

1. A portable electronic device comprising;
   a housing,
   a chemical sensor sensitive to a concentration value of a component in a sample of air, said chemical sensor being configured and structured to perform a chemical measurement supplying results indicative of said concentration value,
   a chemical sensor processing unit connected to said chemical sensor, and
   at least one contextual sensor not including chemical, temperature and humidity sensors,
   wherein said chemical sensor is integrated into said housing,
   wherein said at least one contextual sensor is arranged within said housing and/or configured and structured to communicate directly or indirectly with the portable electronic device, wherein said portable electronic device is configured and structured to link an output from said at least one contextual sensor to a local and/or remote interpretation processor, which interpretation processor is configured and structured to generate a constraint or correlation set for restricting interpretations of said chemical measurement results, wherein said portable electronic device is configured and structured to transfer said constraint or correlation set from said local and/or remote interpretation processor to the chemical sensor processing unit, wherein said chemical sensor processing unit is configured to determine said concentration value of said component using said chemical measurement, and using said constraint or correlation set to restrict interpretations of said chemical measurement results by one or more of altering a result of said chemical measurement to match the constraints and correlations as imposed by the input from the interpretation processor or removing uncertainties or false measurements from the results of the chemical measurement, and wherein said interpretation processor is configured and structured to convert inputs as provided by the one or more contextual sensors into the constraint or correlation set including a constraint vector representing a known response or signature or emission profile of the chemical sensor in the presence of one of an object, sound, location information identified from the inputs provided by the one or more contextual sensors.

2. The portable electronic device of claim 1, wherein said contextual sensor is selected from the group consisting of an image capturing device, a sound capturing device, an electromagnetic wave antenna, an infrared sensor, a proximity sensor, a location sensitive device, an orientation sensitive device, and a motion sensitive device.

3. The portable electronic device of claim 1, wherein said local and/or remote interpretation processor includes a processor extracting signals from the contextual sensor output representative of an abstract object or event in the vicinity of the portable device at the time of said chemical measurement.

4. The portable electronic device of claim 3, wherein said local and/or remote interpretation processor includes a processor located remotely from the portable electronic device and linked through a telecommunication link to the portable electronic device.

5. The portable electronic device of claim 1, wherein said local and/or remote interpretation processor includes a processor for image, sound/speech, geographical location, motion, proximity, orientation, or event recognition.

6. The portable electronic device of claim 1, wherein the at least one contextual sensor is linked to a pre-capture system for initiating signal capture and storage prior to the performance of said chemical measurement.

7. The portable electronic device of claim 1, further including a precision unit for requesting said constraint or correlation set from a contextual sensor measurement.

8. The portable electronic device of claim 1, wherein the chemical sensor comprises a metal-oxide sensing material.

9. The portable electronic device of claim 1, wherein the chemical sensor is integrated onto a common substrate including CMOS circuitry.

10. The portable electronic device of claim 1, selected from the group consisting of a mobile phone, a handheld computer, an electronic reader, a tablet computer, a game controller, a pointing device, a photo or a video camera, a digital music player, an electronic wrist watch, a headset, and a computer peripheral.

11. The portable electronic device of claim 1, wherein the chemical sensor processing unit is configured and structured to one of:
use the constraint vector in an analysis of the measurement of the chemical sensor thereby limiting variables to be determined; or
design a filter applied to the measurement of the chemical sensor.

12. A method of operating a portable electronic device which comprises a housing, a chemical sensor sensitive to a concentration value of a component in a sample of air, a chemical sensor processing unit connected to said chemical sensor, and at least one contextual sensor not including chemical, temperature and humidity sensors, wherein said chemical sensor is integrated into said housing, and wherein said at least one contextual sensor is arranged within said housing and/or configured and structured to communicate directly or indirectly with the portable electronic device, the method comprising steps of;
performing a chemical measurement supplying results indicative of said concentration value of said component,
performing a contextual measurement using said at least one contextual sensor and linking an output from said at least one contextual sensor to a local and/or remote interpretation processor, which interpretation processor is configured and structured to generate a constraint or correlation set for restricting interpretations of said chemical measurement results,
transferring said constraint or correlation set from said local and/or remote interpretation processor to said chemical sensor processing unit,
determining said concentration value of said component using said chemical measurement, and using said constraint or correlation set to restrict interpretations of said chemical measurement results by one or more of altering a result of said chemical measurement to match the constraints and correlations as imposed by the input from the interpretation processor or removing uncertainties or false measurements from the results of the chemical measurement, and
wherein said interpretation processor is configured and structured to convert inputs as provided by the one or more contextual sensors into the constraint or correlation set including a constraint vector representing a known response or signature or emission profile of the chemical sensor in the presence of one of an object, sound, location information identified from the inputs provided by the one or more contextual sensors.

13. A portable electronic device comprising;
a housing,
a chemical sensor sensitive to a concentration value of a component in a sample of air, said chemical sensor being configured and structured to perform a chemical measurement supplying results indicative of said concentration value,
a chemical sensor processing unit connected to said chemical sensor, and
at least one contextual sensor selected from a group consisting of an image capturing device, a sound capturing device, an electromagnetic wave antenna, an infrared sensor, a proximity sensor, a location sensitive device, an orientation sensitive device, and a motion sensitive device, wherein said chemical sensor is integrated into said housing, wherein said at least one contextual sensor is arranged within said housing and/or configured and structured to communicate directly or indirectly with the portable electronic device, wherein said portable electronic device is configured and structured to link an output from said at least one contextual sensor to a local and/or remote interpretation processor, which interpretation processor is configured and structured to generate a constraint or correlation set for restricting interpretations of said chemical measurement results, wherein said portable electronic device is configured and structured to transfer said constraint or correlation set from said local and/or remote interpretation processor to said chemical sensor processing unit, wherein said chemical sensor processing unit is configured to determine said concentration value of said component using said chemical measurement, and using said constraint or correlation set to restrict interpretations of said chemical measurement results by one or more of altering a result of said chemical measurement to match the constraints and correlations as imposed by the input from the interpretation processor or removing uncertainties or false measurements from the results of the chemical measurement, and wherein said interpretation processor is configured and structured to convert inputs as provided by the one or more contextual sensors into the constraint or correlation set including a constraint vector representing a known response or signature or emission profile of the chemical sensor in the presence of one of an object, sound, location information identified from the inputs provided by the one or more contextual sensors.

14. A method of operating a portable electronic device which comprises a housing, a chemical sensor sensitive to a concentration value of a component in a sample of air, a chemical sensor processing unit connected to said chemical sensor, and at least one contextual sensor selected from a group consisting of an image capturing device, a sound capturing device, an electromagnetic wave antenna, an infrared sensor, a proximity sensor, a location sensitive device, an orientation sensitive device, and a motion sensitive device, wherein said chemical sensor is integrated into said housing, and wherein said at least one contextual sensor is arranged within said housing and/or configured and structured to communicate directly or indirectly with the portable electronic device, the method comprising steps of;

performing a chemical measurement supplying results indicative of said concentration value of said component, performing a contextual measurement using said at least one contextual sensor and linking an output from said at least one contextual sensor to a local and/or remote interpretation processor, which interpretation processor is configured and structured to generate a constraint or correlation set for restricting interpretations of said chemical measurement results, transferring said constraint or correlation set from said local and/or remote interpretation processor to said chemical sensor processing unit, determining said concentration value of said component using said chemical measurement, and using said constraint or correlation set to restrict interpretations of said chemical measurement results by one or more of altering a result of said chemical measurement to match the constraints and correlations as imposed by the input from the interpretation processor or removing uncertainties or false measurements from the results of the chemical measurement, and wherein said interpretation processor is configured and structured to convert inputs as provided by the one or more contextual sensors into the constraint or correlation set including a constraint vector representing a known response or signature or emission profile of the chemical sensor in the presence of one of an object, sound, location information identified from the inputs provided by the one or more contextual sensors.

* * * * *